US011160813B2

(12) United States Patent
Lau et al.

(10) Patent No.: US 11,160,813 B2
(45) Date of Patent: Nov. 2, 2021

(54) COMBINATION THERAPY FOR NONALCOHOLIC STEATOHEPATITIS (NASH) AND LIVER FIBROSIS

(71) Applicant: Modunex Bio Corp., Tortola (VG)

(72) Inventors: Walter Lau, Belmont, CA (US); Christopher Wang, Edison, NJ (US); Shonan Sho, Los Angeles, CA (US)

(73) Assignee: Modunex Bio Corp., Tortola (VG)

( * ) Notice: Subject to any disclaimer, the term of this patent is extended or adjusted under 35 U.S.C. 154(b) by 0 days.

(21) Appl. No.: 16/473,706

(22) PCT Filed: Dec. 28, 2017

(86) PCT No.: PCT/US2017/068728
§ 371 (c)(1),
(2) Date: Jun. 26, 2019

(87) PCT Pub. No.: WO2018/126016
PCT Pub. Date: Jul. 5, 2018

(65) Prior Publication Data
US 2019/0321377 A1 Oct. 24, 2019

Related U.S. Application Data

(60) Provisional application No. 62/439,666, filed on Dec. 28, 2016.

(51) Int. Cl.
*A61K 31/575* (2006.01)
*A61P 1/16* (2006.01)
*A61K 31/4375* (2006.01)
*A61K 31/46* (2006.01)

(52) U.S. Cl.
CPC ........ *A61K 31/575* (2013.01); *A61K 31/4375* (2013.01); *A61K 31/46* (2013.01); *A61P 1/16* (2018.01)

(58) Field of Classification Search
CPC .................................................. A61K 31/375
See application file for complete search history.

(56) References Cited

FOREIGN PATENT DOCUMENTS

| WO | 2016/040860 A1 | 3/2016 | |
|---|---|---|---|
| WO | WO-2016040860 A1 * | 3/2016 | .............. A61P 31/20 |
| WO | 2017/048322 A1 | 3/2017 | |

OTHER PUBLICATIONS

Yang et al., The discovery of MK-0812, a potent and selective CCR2 antagonist, The 233rd ACS National Meeting, Chicago, IL, Mar. 25-29, 2007, available at http://oasys2.confex.com/acs/233nm/techprogram/P1045439.HTM.*

Oh et al, Non-alcoholic fatty liver diseases: update on the challenge of diagnosis and treatment, Clinical and Molecular Pathology 2016; 22:327-335.*
STN document No. 612595371, entered Embase: Nov. 14, 2016.*
BusinessWire, Tobira Therapeutics Announces Clinically and Statistically Significant Improvement in Liver Fibrosis From Phase 2b CENTAUR NASH Trial at One Year. Retrieved online at: https://www.businesswire.com/news/home/20160725005384/en/Tobira-Therapeutics-Announces-Clinically-Statistically-Significant-Improvement. 4 pages, Jul. 25, 2016.
ClinicalTrials.gov, Randomized Global Phase 3 Study to Evaluate the Impact on NASH With Fibrosis of Obeticholic Acid Treatment (Regenerate). Identifier: NCT02548351. Retrieved online at: https://clinicaltrials.gov/ct2/show/NCT02548351. 6 pages, Nov. 20, 2019.
FDA Packaging Label, Ocaliva (obeticholic acid). Retrieved online at: http:www.accessdata.fda.gov. 24 pages, Jan. 2018.
Jacobs, Pharmacology/Toxicology NDA Review and Evaluation, Obeticholic acid. Center for Drug Evaluation and Research, Application No. 207999Orig1s000, Pharmacology Review(s). 229 pages, Nov. 23, 2015.
Kleiner et al., Design and Validation of a Histological Scoring System for Nonalcoholic Fatty Liver Disease. Hepatology. Jun. 2005;41(6):1313-21.
Lefebvre et al., Antifibrotic Effects of the Dual CCR2/CCR5 Antagonist Cenicriviroc in Animal Models of Liver and Kidney Fibrosis. PLoS One. Jun. 27, 2016;11(6):e0158156, 19 pages.
Machado et al., Mouse models of diet-induced nonalcoholic steatohepatitis reproduce the heterogeneity of the human disease. PLoS One. May 27, 2015;10(5):e0127991, 16 pages.
Mehta, Clinical Review. Obeticholic acid (INNT-747), Ocaliva. Center for Drug Evaluation and Research. Application No. 207999Orig1s000, Medical Review(s). 304 pages, Jun. 27, 2015.
Neuschwander-Tetri et al., Farnesoid X nuclear receptor ligand obeticholic acid for non-cirrhotic, non-alcoholic steatohepatitis (FLINT): a multicentre, randomised, placebo-controlled trial. Lancet. Mar. 14, 2015;385(9972):956-65.

(Continued)

*Primary Examiner* — Svetlana M Ivanova
(74) *Attorney, Agent, or Firm* — McCarter & English, LLP; Steven G. Davis; Wei Song

(57) ABSTRACT

The innovation is directed to a method for treating a CCR5 and/or CCR2 mediated disease such as nonalcoholic steatohepatitis (NASH) comprising administering an effective amount of a C—C Chemokine receptor 5 (CCR5) antagonist (e.g., maraviroc or vicriviroc or cenicriviroc) and/or an effective amount of a C—C Chemokine receptor 2 (CCR2) antagonist, or a CCR5/CCR2 antagonist together with an effective amount of farnesoid X receptor (FXR) agonist (e.g., obeticholic acid (OCA)). An "effective amount" can be a regular clinical dose of either agent alone or a reduced dose of the FXR receptor agonist and/or the CCR5/CCR2 antagonist. The combination is effective to treat NASH with (1) enhanced efficacy and (2) substantial reduction of side effects, particularly those associated with administration of OCA or its analogues, namely less effect on liver enzyme elevation, and less severity and frequency of pruritus (3). The fixed dose combination provides for better efficacy and safety profile.

4 Claims, 8 Drawing Sheets

(56) References Cited

OTHER PUBLICATIONS

Orgeta Gonzalez et al., The effects of Maraviroc on liver fibrosis in HIV/HCV co-infected patients. Abstracts of the HIV Drug Therapy Glasgow Congress 2014. J Int AIDS Soc. Nov. 2, 2014;17(4 Suppl 3):19643, Abstract P111, 1 page.
Perez-Martinez et al., Maraviroc, a CCR5 antagonist, ameliorates the development of hepatic steatosis in a mouse model of non-alcoholic fatty liver disease (NAFLD). J Antimicrob Chemother. Jul. 2014;69(7):1903-10.
Seki et al., CCR1 and CCR5 promote hepatic fibrosis in mice. J Clin Invest. Jul. 2009;119(7):1858-70.
Seki et al., CCR2 promotes hepatic fibrosis in mice. Hepatology. Jul. 2009;50(1):185-97.
Oh et al., Non-alcoholic fatty liver diseases: update on the challenge of diagnosis and treatment. Clin Mol Hepatol. Sep. 2016;22(3):327-335.

\* cited by examiner

COMBINATION THERAPY FOR NONALCOHOLIC STEATOHEPATITIS (NASH) AND LIVER FIBROSIS

RELATED APPLICATIONS

This application is a 35 U.S.C. § 371 national stage filing of International Application No. PCT/US2017/068728, filed Dec. 28, 2017, which claims the benefit of U.S. Provisional Application Ser. No. 62/439,666, filed Dec. 28, 2016. The entire teachings of each of the foregoing applications are incorporated herein by reference.

BACKGROUND OF THE INVENTION

Nonalcoholic steatohepatitis (NASH) is an insidious and slow-progressing disease having a significant impact on quality of life. It can eventually result in cirrhosis of the liver, decompensated liver disease and/or hepatocelluar carcinoma. The essential feature is constant insults from steatosis, release of inflammatory chemokines, inflammation and fibrosis. The fibrosis associated with inflammation is the key driver for disease progression. Multiple drugs with diverse mechanisms have been tested in clinical trials, however, no effective treatments have been approved yet.

There are a number of new molecules now in different stages of clinical development for NASH, but only marginal/modest effects have been reported (1, 2).

CCR5 antagonists were initially developed as an HIV entry inhibitor for treatment of HIV. Maraviroc is the first molecule approved for this indication. It has been shown that liver steatosis is associated elevation of chemokines including CCL5/rantes and its receptor CCR5 (3). Other ligands for CCR5 include CCL3, CCL4, CCL7, CCL13, and CCL16. Inhibition of CCR5 by maraviroc has been shown to be effective in an animal model for reducing NAS score and fibrosis (4). Reducing liver fibrosis has been observed in HIV patients with HCV infection while receiving maraviroc treatment (5). Recent studies indicated that cenicriviroc, targeting both CCR5 and CCR2, has a marginal effect on NASH and a relatively more significant effect on fibrosis (2, 6). Cenicriviroc is under clinical development for NASH. Another clinical stage CCR5 antagonist is vicroviroc. The primary efficacy of CCR5 antagonists on NASH is mainly reflected in its effect on fibrosis with a lessor effect on the NAS score (2). CCR2 has been reported as an important player in liver fibrosis as well (7).

Obeticholic acid (OCA) is a semi-synthetic bile acid analogue with a chemical structure of 6 α-ethyl-chemodeoxycholic acid. The mechanism of action is via activating the farnesoid X receptor (FXR). It is undergoing clinical development as a pharmaceutical agent for several liver diseases and related disorders. It has been approved for treatment of primary biliary cholangitis by the US FDA in 2016 (8). The clinical program for NASH is under phase 3 development.

The preclinical toxicology studies have shown that the target system of toxicity of OCA was the hepatobiliary system. In a 26-week oral toxicity study in rats, treatment with OCA produced changes in clinical chemistry parameters (e.g. increases in ALT, AST and ALP), increased liver weight and bile duct hyperplasia (9). In a 9-month oral toxicity study in dogs, OCA produced clinical signs of toxicity that could be associated with liver function (yellow discoloration of skin, mucous membrane, and eyes) and elevated ALT levels. Liver toxicity was also reported in clinical trials; exposure-adjusted incidence for all serious and otherwise clinically significant liver-related adverse reactions and isolated elevations in liver biochemical test, per 100 patient exposure years (PEY) were: 5.2 in a 10 mg group, 19.8% in a 25 mg group and 54.5% in 50 mg group compared to 2.4 in the placebo group (10).

OCA has been shown to cause dose related side effects, including pruritus and reduction of HDL. Pruritus is one of most common adverse events for OCA; the frequency has been reported to be up to 80%; also dose related discontinuations due to pruritus were also reported. Severe pruritus was listed as one of warnings and precautions in the US package insert for OCA; sometimes a dosage reduction and/or temporary dosing interruption will be needed (8). There are a few other new molecular entities targeting FXR under different stages of development.

Both clinical and preclinical data indicated that there is modest to moderate efficacy achieved by targeting via CCR5 or CCR2/5 antagonist or the FXR pathway using OCA as a FXR agonist (1,2). This could be one of the reasons why OCA is under clinical testing with 2000 NASH patients (10) with a readout following 18 months treatment. Pre-clinically, the efficacy is also modest. Preclinical and human data indicated that targeting CCR5, or CCR2/5 using a CCR5, or CCR2/5 antagonist has been effective in reducing fibrosis but a much smaller effective is observed with the NAS score or steatosis (2). NASH is a chronic disease and most patients have benign causes of the disease; for this reason, it is imperative to have a treatment option that is very safe in addition to being efficacious. Therefore, there is a need for improved methods of treating NASH/liver fibrosis to increase the overall efficacy and improving the safety profile.

SUMMARY OF THE INVENTION

It has now been found here that the combination of a CCR5 or CCR2 inhibitor or molecule(s) targeting CCR2/5 and a FXR agonist is more effective in treating NASH with fewer side effects than either agent alone, even when FXR is given at a dose that is lower than full dose.

Specifically, the following observations were made when the CCR5 inhibitor maraviroc and the FXR agonist obeticholic acid (OCA) were each administered alone and in combination in a mouse model of NASH (see the Exemplification):

- The combination therapy was more effective than either single agent alone in reducing the NAS score (FIG. 1A).
- The combination therapy was more effective than either single agent alone in reducing liver fibrosis (FIG. 3A).
- The combination therapy was more effective than either single agent alone in reducing the liver inflammation score (FIG. 4A).
- The combination therapy was more effective than either single agent alone in reducing the liver hepatocyte ballooning score (FIG. 5A), and a synergistic effect on ballooning was shown. Furthermore, an absence of ballooning was observed when half the doses of both agents were administered.
- The combination therapy was more effective than either single agent alone in reducing liver steatosis score (FIG. 6A).
- Dose Reduction of OCA (half dose or more greater reduction of OCA) with a full dose CCR5/CCR2 antagonist can produce adequate efficacy but reduced toxicity in long term chronic treatment settings.

Moreover, the elevation in AST and ALP liver enzymes observed in mice treated with OCA was not observed in the mice treated with both MVC and OCA (FIG. 7A-8A), indicating that undesirable liver toxicity caused by OCA could be mitigated by concurrent treatment with MVC. Based on these discoveries, methods of treating NASH and other C—C Chemokine receptor 5 (CCR5) mediated (and/or CCR2 mediated) inflammatory diseases with a CCR5 antagonist (and/or a CCR2 antagonist) and an FXR agonist (such as OCA) are disclosed herein. Similar observations were noted when the CCR2 antagonist MK-0812 was administered instead of the CCR5 antagonist MCV (FIGS. 7B and 8B), or treatment with CCR2/5 using a combination of the CCR5 inhibitor maraviroc and the CCR2 antagonist MK-0812 (data not shown).

One embodiment of the invention is a method of treating a human patient with a C—C Chemokine receptor 5 (CCR5) mediated inflammatory disease; a CCR2 receptor mediated inflammatory disease; or a CCR2/5 receptor mediated inflammatory disease. The method comprises administering an effective amount of a CCR5 antagonist (such as maraviroc, vicriviroc, or cenicriviroc); or a CCR2 antagonist such as (MLN-1202 (AB), CCX-140, PF-4136309, JNJ-17166864, AZD-2423, INCB-003284, BMS-741672, MK-0812, PF-04634817); or a CCR2/5 antagonist such as (cenicriviroc) and an effective amount of a farnesoid X receptor (FXR) agonist to the patient.

Another embodiment of the invention is a method of treating a human patient with a C—C Chemokine receptor 5 (CCR5) mediated inflammatory disease, comprising administering to the patient an effective amount of a CCR5 antagonist and an effective amount of a farnesoid X receptor agonist. Another embodiment of the invention is a method of treating a human patient with a C—C Chemokine receptor 2 (CCR2) mediated inflammatory disease, comprising administering to the patient an effective amount of a CCR2 antagonist and an effective amount of a farnesoid X receptor agonist. Another embodiment of the invention is a method of treating a human patient with a C—C Chemokine receptor CCR2/5 mediated inflammatory disease, comprising administering to the patient an effective amount of a CCR2/CCR5 antagonist and an effective amount of a farnesoid X receptor agonist.

Another embodiment of the invention is a method for treating an FXR mediated disease such as NASH or biliary cirrhosis or applicable indications by an FXR agonist. The method comprises administering an effective amount of farnesoid X receptor (FXR) agonist in combination with an effective amount of a CCR5 antagonist to improve the safety profiles of FXR agonist and/or efficacy.

Another embodiment of the invention is a method for treating an FXR mediated disease such as NASH or biliary cirrhosis or applicable indications by FXR agonist. The method comprises administering an effective amount of farnesoid X receptor (FXR) agonist in combination with an effective amount of a CCR2 antagonist to improve the safety profiles of FXR agonist and/or efficacy.

Another embodiment of the invention is a method for treating an FXR mediated disease such as NASH or biliary cirrhosis or applicable indications by FXR agonist. The method comprises administering an effective amount of farnesoid X receptor (FXR) agonist in combination with an effective amount of a CCR2/5 antagonist to improve the safety profiles of FXR agonist and/or efficacy.

The disclosed combination therapy is effective to treat CCR5 and/or CCR2 mediated inflammatory diseases or FXR mediated diseases such as NASH with (1) enhanced efficacy, and (2) substantial reduction of side effects, especially associated with administration of OCA or its analogues, namely less effect on liver enzyme elevation, and less severity and frequency of pruritus, and (3) the full dose of the FXR agonist can be reduced to achieve combined efficacy while reducing side effects. With the disclosed combination therapy, it is anticipated a lower dose of OCA would be needed to achieve comparable efficacy than when OCA is administered alone.

DETAILED DESCRIPTION OF THE INVENTION

Figure 1A:
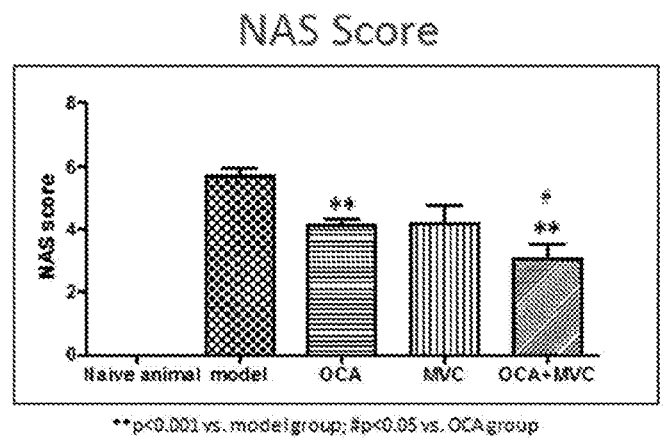
FIG. 1A is a bar graph showing that OCA and MVC administered alone in a mouse model of NASH were associated with a modest reduction of NAS scores, but a more substantial effect was obtained when both OCA and MCV were administered in combination such as full dose combination and half dose combination.
Figure 1B:
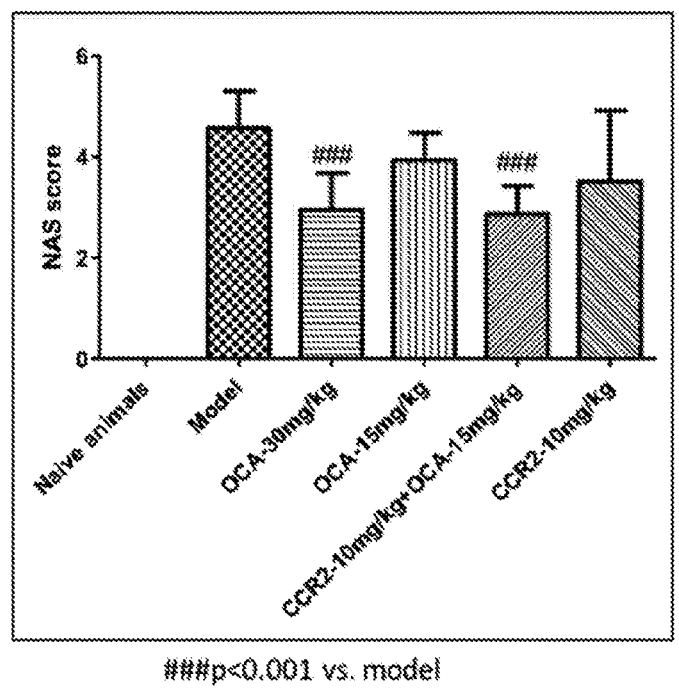
FIG. 1B is a bar graph showing that OCA and CCR2 antagonist (MK-0812) administered alone in a mouse model of NASH were associated with a modest reduction of NAS scores, but a more substantial effect was obtained when both OCA and MK-0812 were administered in combination. A particularly noteworthy effect was noted when half of the dose of OCA at 15 mg/mg instead of 30 mg/kg was administered with MK-0812 at (10 mg twice daily), considering that the CCR2 antagonist alone or a half dose of OCA have little effect

A "C—C Chemokine receptor 5 (CCR5) mediated inflammatory disease" refers to a disease or condition characterized by inflammation caused at least in part by aberrant activity of CCR5-axis (including ligands of CCR5 such as the CCL3, CCL4, CCL5, CCL X and CCR5 receptor) or whose symptoms can be alleviated, at least in part, by inhibition of CCR5. Examples of CCR5 mediated inflammatory disorders include nonalcoholic steatohepatitis (NASH), fibrotic diseases (e.g., liver fibrosis, kidney fibrosis and lung fibrosis) and primary biliary sclerosis. A "C—C Chemokine receptor 2 (CCR2) mediated inflammatory disease" refers to a disease or condition characterized by inflammation caused at least in part by aberrant activity of the CCR2-axis. A "CCR5/CCR2 mediated inflammatory disease" refers to a disease or condition characterized by inflammation caused at least in part by aberrant activity of the CCR5-axis and/or CCR2 axis.

An FXR mediated disease refers to a disease, such as NASH or primary biliary sclerosis, caused, at least in part, by aberrant activity of FXR.

"CCR5/CCR2 antagonist" means a compound which inhibits CCR5 and/or CCR2.

"CCR5 antagonist" means the family of highly homologous species-specific antagonists including maraviroc (MVC), vicriviroc and centiviroc, that inhibits CCR5.

Maraviroc is currently licensed by Pfizer, New York, N.Y. under trade name of Selentry for treatment of HIV indication.

Vicriviroc is a CCR5 antagonist that has been developed by legacy Schering-Plough, currently shelved by Merck/MSD, Kenilworth N.J.

Cenicriviroc is a CCR5 and CCR2 dual antagonist under development for treatment of NASH and HIV by Tobira, South San Francisco, Calif. 94080.

CCR2 antagonist means the family of highly homologous species-specific antagonists that inhibit CCR2 that include: MLN-1202 (AB), CCX-140, PF-4136309, JNJ-17166864, AZD-2423, INCB-003284, BMS-741672, MK-0812 or PF-04634817.

FXR agonists include Obeticholic acid (OCA), a clinical stage compound approved for primary biliary cholangitis by Intercept Pharmaceuticals, 450 W 15th street, Suite 505, floor 5, New York, N.Y. 10011, the OCA is in phase 3 clinical development for NASH. Also included is PX104, an FXR agonist under development by Phenex, Ludwigshafen, Germany, partnered with Gilead, Forest City, Calif.; and AKN-083, being developed by Akarna Therapeutics, to be acquired by Allergan, Irvine, Calif.

This patent also encompasses deuterated versions of a CCR5, CCR2 or CCR2/5 antagonist such as maraviroc and vicriviroc and cenicriviroc. These deuterated CCR5, CCR2 or CCR2/5 antagonists have a mechanism of action via CCR5, CCR2 or CCR2/5 antagonism, similar to the corresponding non-deuterated version of the CCR5, CCR2 or CCR2/5 antagonists respectively.

"Effective amount" refers to the amount of CCR5 antagonist, the amount of CCR2 antagonist or the amount of CCR2/5 antagonist and the amount of FXR agonist which, when administered to a human patient with a CCR5/CCR2 mediated inflammatory disease or an FXR mediated disease, achieves a desired therapeutic effect, e.g., the different CCR5 antagonist is administered at different doses: for maravoric, the dose is between 100 to 300 mg twice daily or 200 to 600 once daily, for vicriviroc, the dose is between 5 to 50 mg once daily, and cenicriviroc is from 50 mg to 400 mg once daily, and MK-0812 from 2 mg to 50 mg once or twice daily. Alternatively, to determine the effective amount, the skilled practitioner can refer to the product label for each approved drug, i.e., the CCR5 antagonist is administered in combination with OCA at either clinically approved dose or lower dose, for example, orally once daily. CCR5 antagonists such as maraviroc or vicriviroc could be administered alone or as a fixed dose combination with OCA. Agents targeting CCR2 OR CCR2/5 could be administered alone or as a fixed dose combination with OCA as well.

OCA at clinically approved 10 mg either administered with a starting dose of 10 mg or titration dose is associated with dose related side effects. The most significant adverse events are pruritus and reduction of HDL. In comparison to 38% from placebo group, 56% and 70% of pruritus were reported in 10 mg once daily and titration regimen, respectively. Severe pruritus was reported in approximately 19-23% of patients receiving OCA (7). A dose related reduction in HDL was also reported. With the combination of a CCR5 antagonist, or a CCR2 antagonist or a CCR5/CCR2 antagonist, it is anticipated a smaller dose of OCA would be needed to achieve comparable efficacy while OCA is administered alone. In this case, a 2-10 mg, 2-8 mg, 2-7 mg, 4-6 mg or 5 mg or a dose less than 10 mg of OCA using in combination with CCR5 antagonist or CCR2 antagonist or CCR2/5 agonist will be the future clinical dose.

All references cited herein are incorporated herein by references.

EXEMPLIFICATION

We have utilized a well validated mice model in which the NASH and fibrosis was induced by sequential induction of diabetes mellitus and a high fat diet (14). On day 2, C59BL/6J mice were injected with streptozocin, then treated with high fat diet from week 4 until week 9. The intervention treatment started from week 5 until week 9. On week 9, these mice were euthanized. The intervention of the NASH and its subsequent disease processes was performed by administration of CCR5 antagonist maraviroc at dose of 45 mg/kg once daily orally and 30 mg/kg of OCA once daily, either alone or in combination for 4 wks.

As shown in FIG. 1A, the CCR5 antagonist maravoric alone had a limited effect on the NAS score and OCA alone caused only a modest reduction of the NAS score. Combination of the CCR5 antagonist with OCA led to a significant reduction of NAS score and was more efficacious than any single agent alone in reducing the NAS score. NAS scores were determined according to the consensus by Nonalcoholic Steatohepatitis Clinical Research Network (13)

Figure 2A:
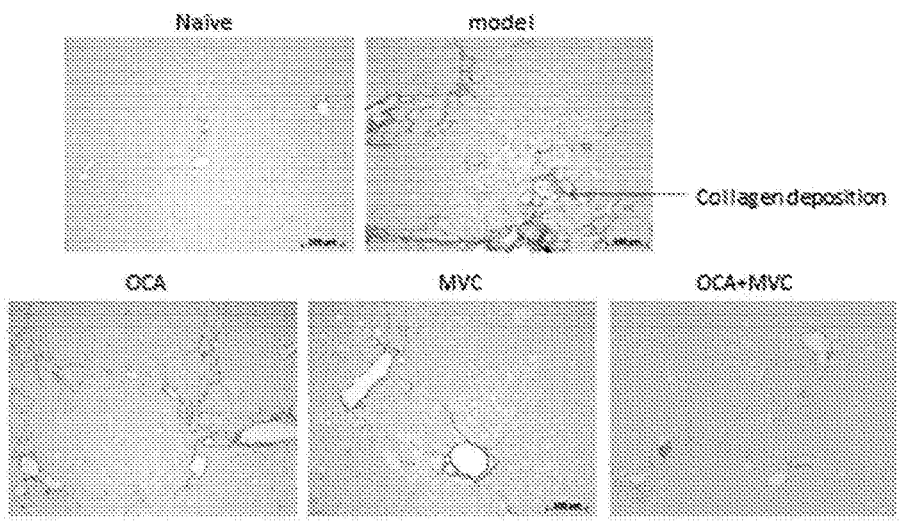
FIG. 2A is a liver histology showing that OCA and MVC administered alone in a mouse model of NASH were associated with a reduction of fibrosis evidenced by staining of collagen, but a more substantial effect was observed when both OCA and MCV were administered in combination.
Figure 2B:
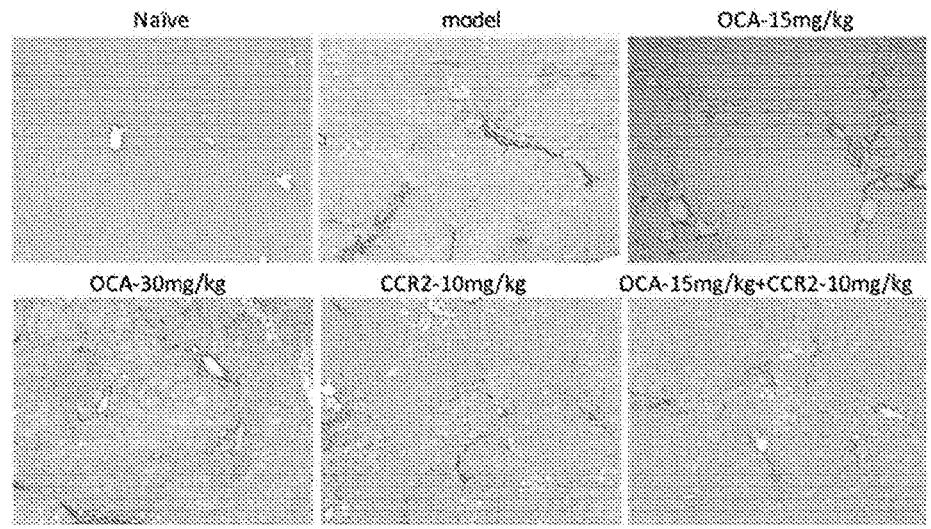
FIG. 2B is a liver histology showing that OCA and MK-0812 administered alone in a mouse model of NASH were associated with a reduction of fibrosis, as evidenced by staining of collagen alone or in combination.
Figure 3A:
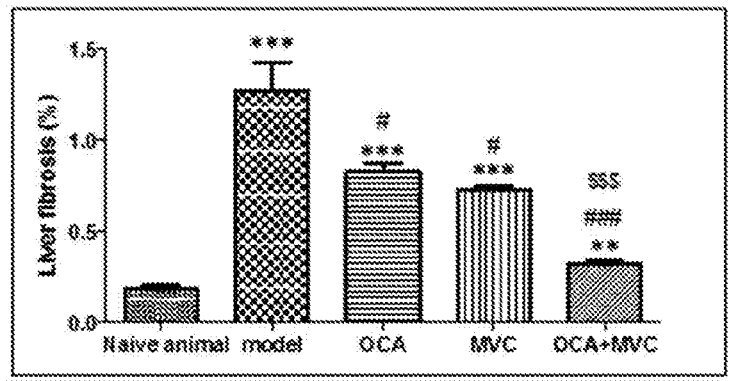
FIG. 3A is a bar graph showing that OCA and MVC administered alone in a mouse model of NASH were associated with a reduction of fibrosis score, but a more substantial effect was observed in when both OCA and MCV were administered in combination.
Figure 3B:
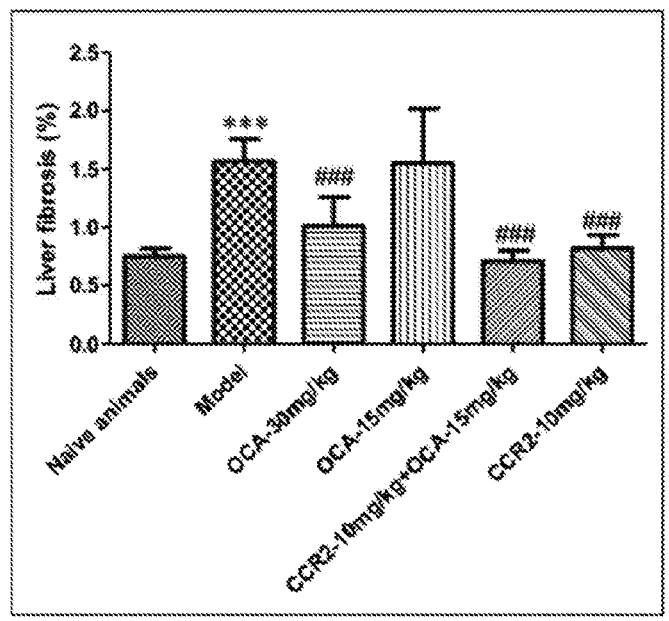
FIG. 3B is a bar graph showing that OCA and MK-0812 administered alone in a mouse model of NASH were associated with a reduction of fibrosis score, but a more substantial effect was observed in when both OCA and MK-0812 were administered in combination. It was worthy to be noted that half of the dose of OCA (at 15 mg/mg instead of 30 mg/kg) was administered with MK-0812 at (10 mg twice daily).
Figure 4A:
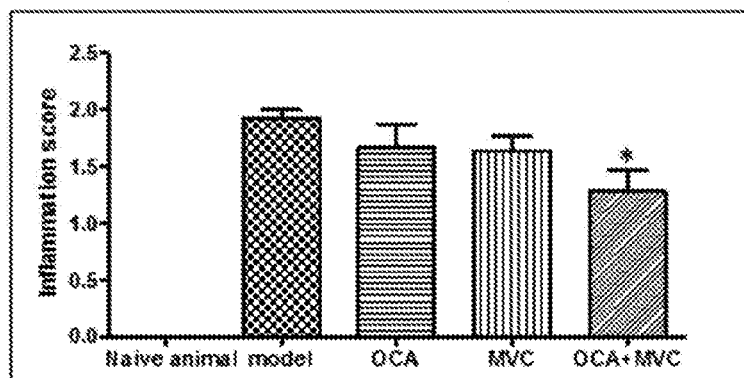
FIG. 4A is a bar graph showing that OCA and MVC administered alone in a mouse model of NASH were associated with a reduction of liver inflammation, but a more substantial effect was obtained when both OCA and MCV were administered in combination.
Figure 4B:
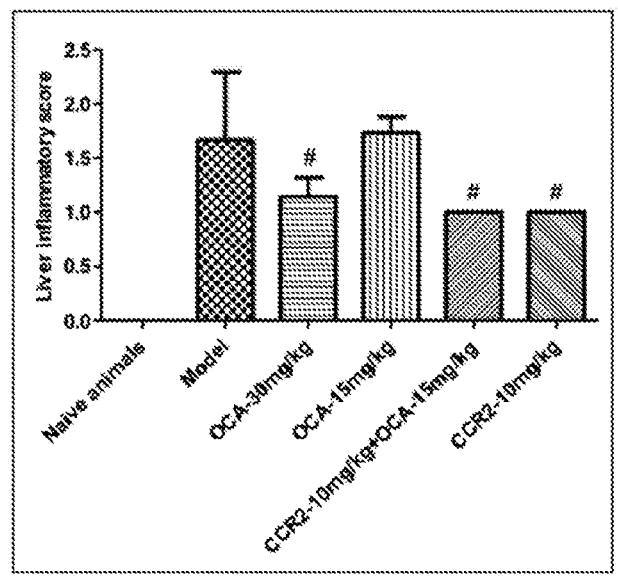
FIG. 4B is a bar graph showing that OCA and MK-0812 administered alone in a mouse model of NASH were associated with a reduction of liver inflammation, but a more substantial effect appeared when both OCA and MK-0812 were administered in combination.
Figure 5A:
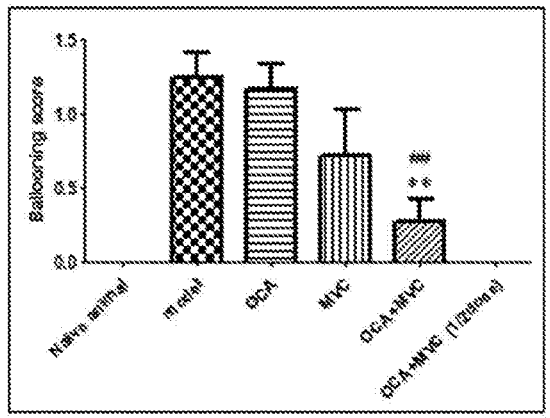
FIG. 5A is a bar graph showing that in an mouse model of NASH, MVC was associated with reduction of hepatocyte ballooning score, but a more substantial effect was observed when both OCA and MCV were administered in combination. Only a marginal effect of OCA on hepatocyte ballooning was noted. When both MCV and OCA are used, the effect on ballooning is greater than the single agent alone, Furthermore, surprisingly when both MCV and OCA were administered half dose, no ballooning was detected.
Figure 5B:
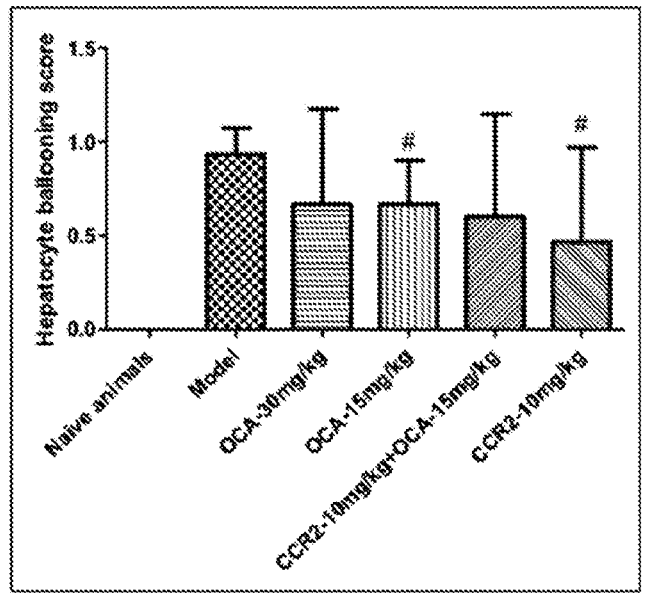
FIG. 5B is a bar graph showing that in an mouse model of NASH, both MK-0812 and OCA were associated with a reduction of hepatocyte ballooning score.
Figure 6A:
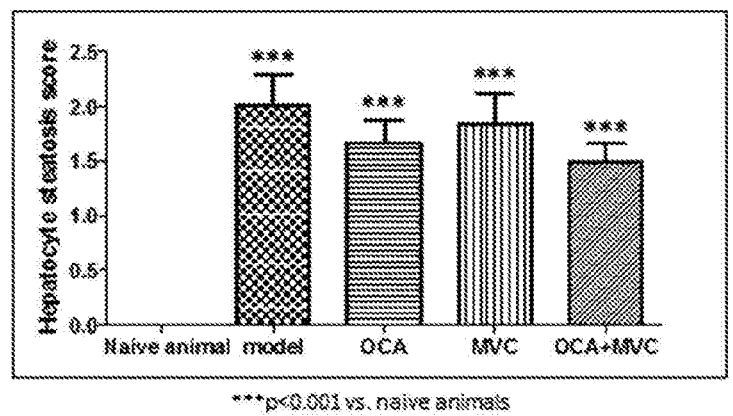
FIG. 6A is a bar graph showing that OCA in a mouse model of NASH was associated with a reduction of steatosis, whereas only a marginal effect on steatosis was observed with MVC alone. A more substantial effect on steatosis was obtained when both OCA and MCV were administered in combination.
Figure 6B:
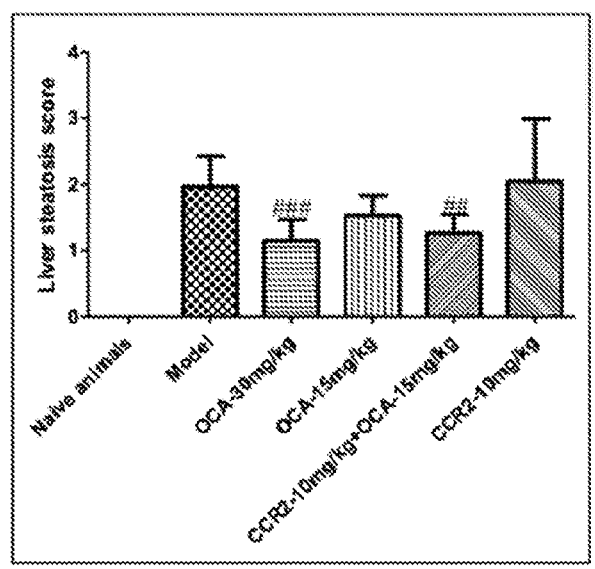
FIG. 6B is a bar graph showing that OCA in a mouse model of NASH was associated with a reduction of steatosis, whereas no apparent effect on steatosis was observed with MK-0812 alone or with half dose of OCA. But the combination of a half-dose of OCA with MK-0812 is as effective as full dose of OCA.
Figure 7A:
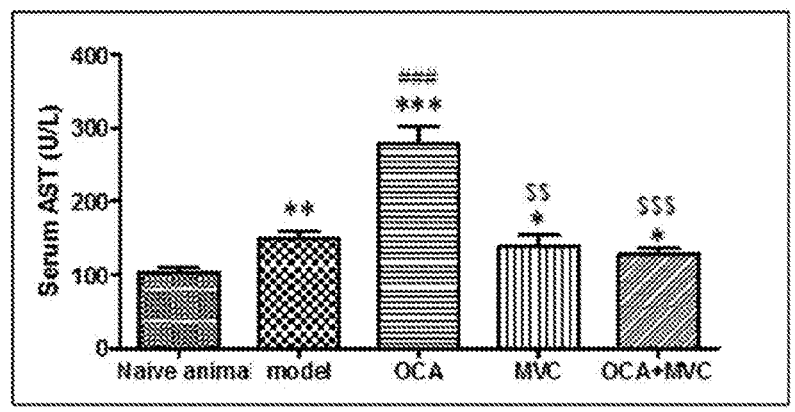
FIG. 7A is a bar graph showing that administration of OCA alone in a mouse model of NASH was associated with elevation of the liver enzyme AST. This adverse effect was not observed in mice treated with MVC alone or with OCA and MVC. The difference of AST between mice treated with OCA and mice treated with OCA/MVC is statistically significant.
Figure 7B:
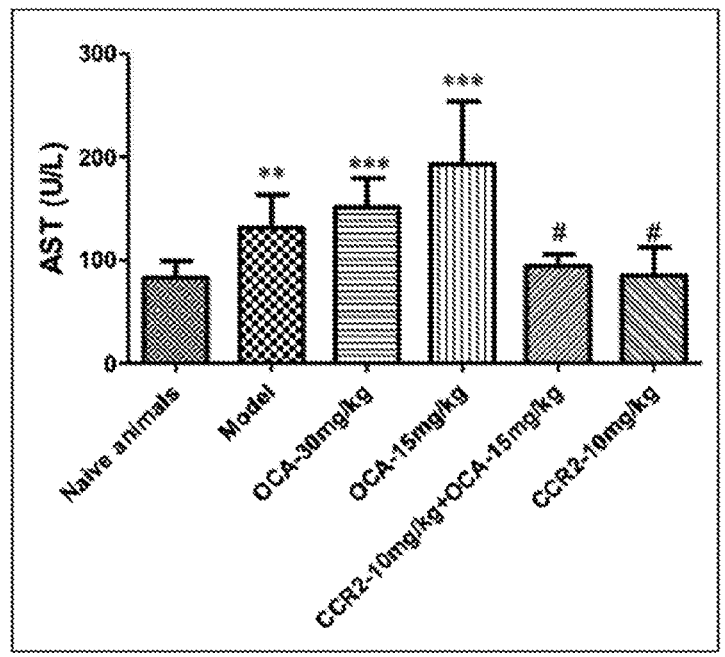
FIG. 7B is a bar graph showing that administration of OCA alone in a mouse model of NASH was associated with elevation of the liver enzyme AST. This adverse effect was not observed in mice treated with MK-0812 alone or with OCA and MK-0812. The difference of AST between mice treated with OCA and mice treated with OCA/MK-0812 is statistically significant.
Figure 8A:
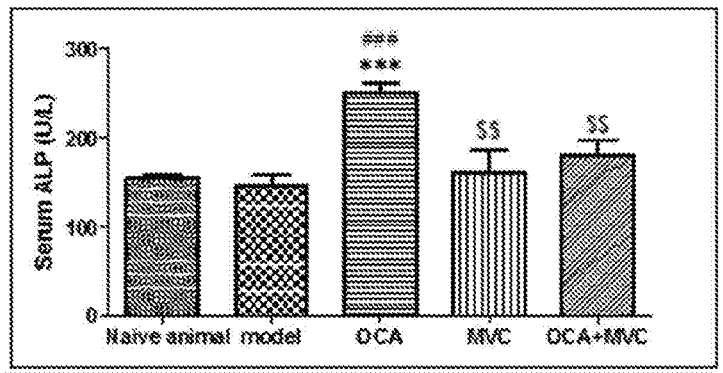
FIG. 8A is a bar graph showing that OCA administered alone in a mouse model of NASH was associated with elevation of the liver enzyme ALP but not in mice treated with MVC or with OCA and MVC. The difference of ALP between mice treated with OCA and mice treated with OCA/MVC is statistically significant.
Figure 8B:
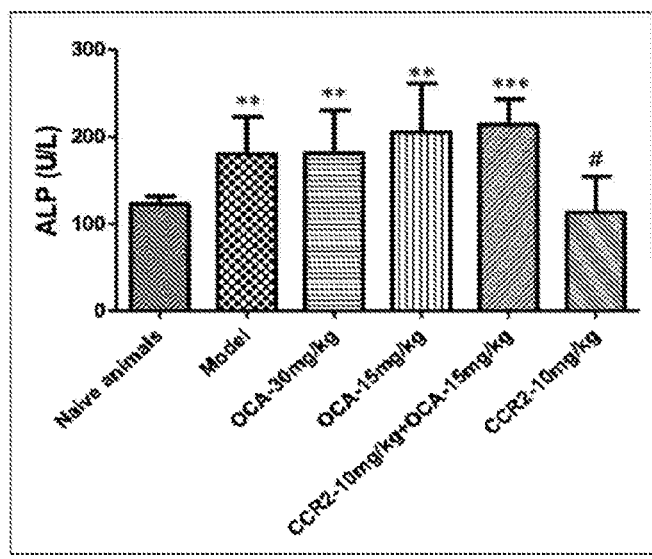
FIG. 8B is a bar graph showing that OCA administered alone in a mouse model of NASH was associated with elevation of the liver enzyme ALP but not in mice treated with MK-0812.

As shown in FIG. 2A, both the CCR5 antagonist maraviroc and OCA were effective in reducing fibrosis, as evidenced by collagen stain (FIG. 2A). Based on this evidence, maraviroc is more effective than OCA in reducing fibrosis. Combination of the CCR5 antagonist with OCA led to a significant effect on reduction of fibrosis. Fibrosis scores were determined according to the consensus by Nonalcoholic Steatohepatitis Clinical Research Network (13). As shown in FIG. 3A, the effect on fibrosis was also quantified by a fibrosis score, and the combination of maraviroc and OCA led to approximately an 80% reduction of fibrosis score. As shown in FIG. 4A, the combination of OCA and MVC alone were associated with a reduction of liver inflammation, but a more substantial effect was observed when both OCA and MCV were administered in combination. As shown in FIG. 5A, MVC was associated with a reduction of the hepatocyte ballooning score, but a more substantial effect was observed when both OCA and MCV were administered in combination. Only a marginal effect of OCA on hepatocyte ballooning was noted. As shown in FIG. 6A, OCA was associated with a modest reduction of steatosis, whereas only marginal effect on steatosis was noted with MVC. A more substantial effect on steatosis was obtained in when both OCA and MCV were administered in combination. Comparable results were obtained when CCR2 antagonist like MK-0812 was used (FIG. 3B to 7B).

Treatment with OCA alone produced changes in clinical chemistry parameters (e.g. increases in ALT, AST and ALP), increased liver weight and bile duct hyperplasia in preclinical animal study and the safety margin relative to recommended human dose is only 2.3 fold (8). Liver toxicity was also reported in clinical trials; exposure-adjusted incidence for all serious and otherwise clinically significant liver-related adverse reactions and isolated elevations in liver biochemical test, per 100 patient exposure years (PEY) were: 5.2 in 10 mg group, 19.8% in 25 mg group and 54.5% in 50 mg group compared to 2.4 in the placebo group (9). In this study, treatment with OCA produced AST and ALP elevation, but this elevation was not observed in the mice treated with both MVC and OCA (FIGS. 7A-8A), and similar findings were noted in CCR2 antagonist MK-0812, indicating that undesirable liver toxicity by OCA could be mitigated by concurrent treatment with MVC or MK-0812.

NON-PATENT CITATIONS

References

1. Neuschwander-Tetri B A, Sanyal A J, Lavine J E, et al. Farnesoid X nuclear receptor ligand obeticholic acid for non-cirrhotic, non-alcoholic steatohepatitis (FLINT):a multicentre, randomised, placebo-controlled trial. *Lancet* 2015; 385: 956-65.
2. http://www.businesswire.com/news/home/20160725005384/en/Tobira-Therapeutics-Announces-Clinically-Statistically-Significant-Improvement
3. Seki E[1], De Minicis S, Gwak G Y, Kluwe J, Inokuchi S, Bursill C A, Llovet J M, Brenner D A, Schwabe R F, CCR1 and CCR5 promote hepatic fibrosis in mice. *J Clin Invest.* 2009 July; 119(7):1858-70
4. Laura Pérez-Martinez, Patricia Përez-Matute, Javier Aguilera-Lizarraga, et e al: Maraviroc, a CCR5 antagonist, ameliorates the development of hepatic steatosis in a mouse model of non-alcoholic fatty liver disease (NAFLD), J. Antimicrob. Chemother. (2014)doi:10.1093/jac/dku071
5. Gonzalez E O, Boix V, Deltoro M G, Aldeguer J L, Portilla J, et al: The effects of Maraviroc on liver fibrosis in HIV/HCV co-infected patients. *J Int AIDS Soc.* 2014 Nov. 2; 17(4 Suppl 3):19643. doi: 10.7448/IAS.17.4.19643.
6. Lefebvre E, Moyle G, Reshef R, Richman L P, Thompson M, Hong F, Chou H L, Hashiguchi T, Plato C, Poulin D, Richards T, Yoneyama H, Jenkins H, Wolfgang G, Friedman S L. Antifibrotic Effects of the Dual CCR2/CCR5 Antagonist Cenicriviroc in Animal Models of Liver and Kidney Fibrosis. PLoS One. 2016 Jun. 27; 11(6): e0158156. doi: 10.1371/journal.pone.0158156.
7. Seki E, de Minicis S, Inokuchi S, Taura K, Miyai K, van Rooijen N, Schwabe R F, Brenner D A. *CCR2 promotes hepatic fibrosis in mice Hepatology.* 2009 July; 50(1): 185-97. doi: 10.1002/hep.22952
8. US label of Obeticholic Acid (Oacliva). http://www.accessdata.fda.gov/drugsatfda_docs/nda/2016/207999Orig1s000Lbl.pdf
9. Summary of Pharmacology Review for Obeticholic Acid (Ocaliva) http://www.accessdata.fda.gov/mwg internal/de5fs23hu73ds/progress?id=WFZ3PwF4uCkU8IF_46n3pQy0kvZdamy5gZ6wtD5mqUk,
10. Summary of Medical Review for Obeticholic Acid (Ovaliva). http://www.accessdata.fda.gov/mwg-internal/de5fs23hu73ds/progress?id=mus83V849Br8KocyHQk176o-VDoGe2hfO7NzsYxAC7M,
11. Randomized Global Phase 3 Study to Evaluate the Impact on NASH With Fibrosis of Obeticholic Acid Treatment (REGENERATE):https://clinicaltrials.gov/ct2/show/NCT02548351
12. Obeticholicacid phase 3 study in NASH: https://clinicaltrials.gov/ct2/show/NCT02548351
13. Kleiner D E, Brunt E M, Van Natta M, Behling C, Contos M J, Cummings O W, Ferrell L D, Liu Y C, Torbenson M S, Unalp-Arida A, Yeh M, McCullough A J, Sanyal A J; Nonalcoholic Steatohepatitis Clinical Research Network. Design and validation of a histological scoring system for nonalcoholic fatty liver disease. Hepatology. 2005 June; 41(6):1313-21.

14. Machado M V, Michelotti G A, Xie G, de Almeida T P, Boursier J, Bohnic B, et al. (2015) Mouse Models of Diet-Induced Nonalcoholic Steatohepatitis Reproduce the Heterogeneity of the Human Disease. PLoS ONE 10(5): e0127991. doi:10.1371/journal.pone.01279

What is claimed is:

1. A pharmaceutical composition comprising a synergistic amount of a CCR5 antagonist wherein the CCR5 antagonist is maraviroc; and a synergistic amount of a FXR agonist wherein the FXR agonist is OCA.

2. A pharmaceutical composition comprising a synergistic amount of a CCR2 antagonist wherein the CCR2 antagonist is MK-0812; and a synergistic amount of a FXR agonist wherein the FXR agonist is OCA.

3. The pharmaceutical composition of claim 1, additionally comprising a CCR2 antagonist.

4. The pharmaceutical composition of claim 2, additionally comprising a CCR5 antagonist.

* * * * *